United States Patent [19]

Kuhn

[11] Patent Number: 5,364,027
[45] Date of Patent: Nov. 15, 1994

[54] DISPENSER ADAPTED FOR COMBINED CONTINUOUS AND INSTANT OPERATION

[75] Inventor: Petrus H. A. N. Kuhn, Den Haag, Netherlands

[73] Assignee: Sara Lee/DE N.V, Utrecht, Netherlands

[21] Appl. No.: 90,213

[22] PCT Filed: Jan. 16, 1992

[86] PCT No.: PCT/NL92/00009

§ 371 Date: Sep. 16, 1993

§ 102(e) Date: Sep. 16, 1993

[87] PCT Pub. No.: WO92/12802

PCT Pub. Date: Aug. 6, 1992

[30] Foreign Application Priority Data

Jan. 17, 1991 [NL] Netherlands ............ 9100089

[51] Int. Cl.⁵ ............. B05B 9/04; B05B 11/04; A45D 34/02
[52] U.S. Cl. ............. 239/44; 239/34; 239/145; 239/289; 239/327; 239/436; 222/187
[58] Field of Search ............. 239/34, 44, 145, 289, 239/327, 354, 436, 443; 222/187, 192, 211

[56] References Cited

U.S. PATENT DOCUMENTS

| 897,131 | 8/1908 | Owen | 222/187 |
|---|---|---|---|
| 960,008 | 5/1910 | Evans et al. | 222/187 X |
| 2,520,368 | 8/1950 | Landau . | |
| 3,972,473 | 8/1976 | Harrison | 239/34 |
| 4,024,992 | 5/1977 | Schmid | 239/327 X |
| 4,084,732 | 4/1978 | Dearling . | |
| 4,306,679 | 12/1981 | Dusek et al. . | |
| 4,341,348 | 7/1982 | Dearling | 239/34 |
| 4,726,519 | 2/1988 | Muoio | 239/289 X |
| 4,809,914 | 3/1989 | Goncalves . | |

FOREIGN PATENT DOCUMENTS

| 2556242 | 6/1985 | France | 239/289 |
|---|---|---|---|
| 2105562 | 3/1983 | United Kingdom | 239/145 |
| 8808308 | 11/1988 | WIPO | 222/187 |

*Primary Examiner*—Andres Kashnikow
*Assistant Examiner*—William Grant
*Attorney, Agent, or Firm*—Merchant & Gould Smith, Edell, Welter & Schmidt

[57] ABSTRACT

The invention relates to a dispenser (1) comprising a container (2) which is to be partly filled with liquid active substance and has a wall that is at least locally resiliently deformable. The dispenser further comprises two immersion tube channels (9, 10) extending from a point adjacent the bottom of the container up to the top of the container (2), one channel terminating in a spray nozzle (8) and the other channel containing a wick (4) or similar absorbent material and terminating in an evaporation space that communicates with the atmosphere. In further elaboration of the invention, the spray nozzle (8), the evaporation space and at least one of the immersion tube channels (9, 10) can be formed as a single moulding which can be click-fitted in the mouth of the container (2) so as to seal it.

6 Claims, 1 Drawing Sheet

U.S. Patent
Nov. 15, 1994
5,364,027
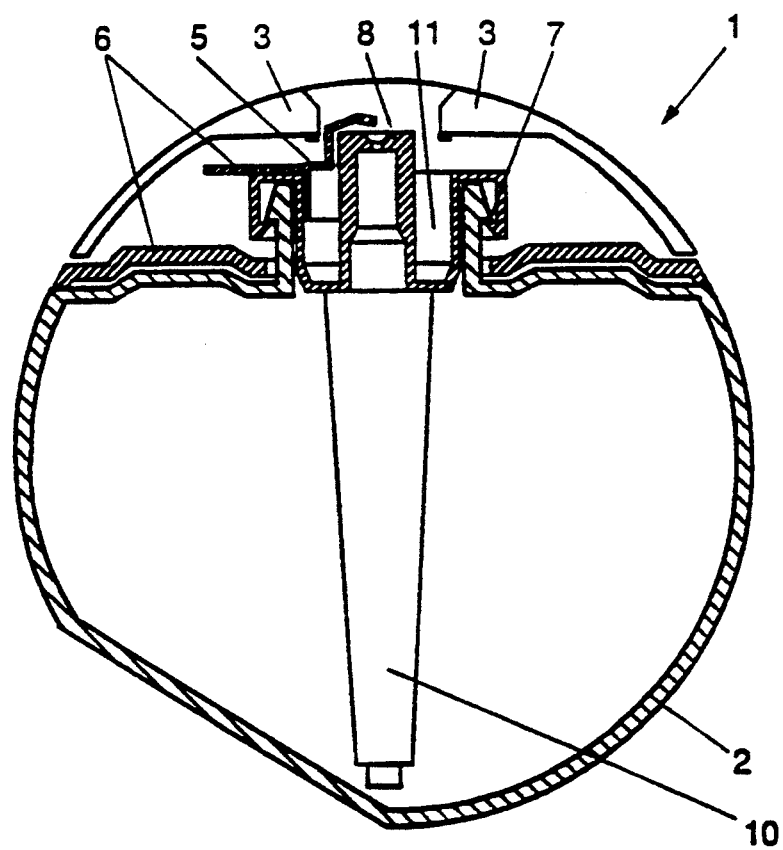
FIG. 1
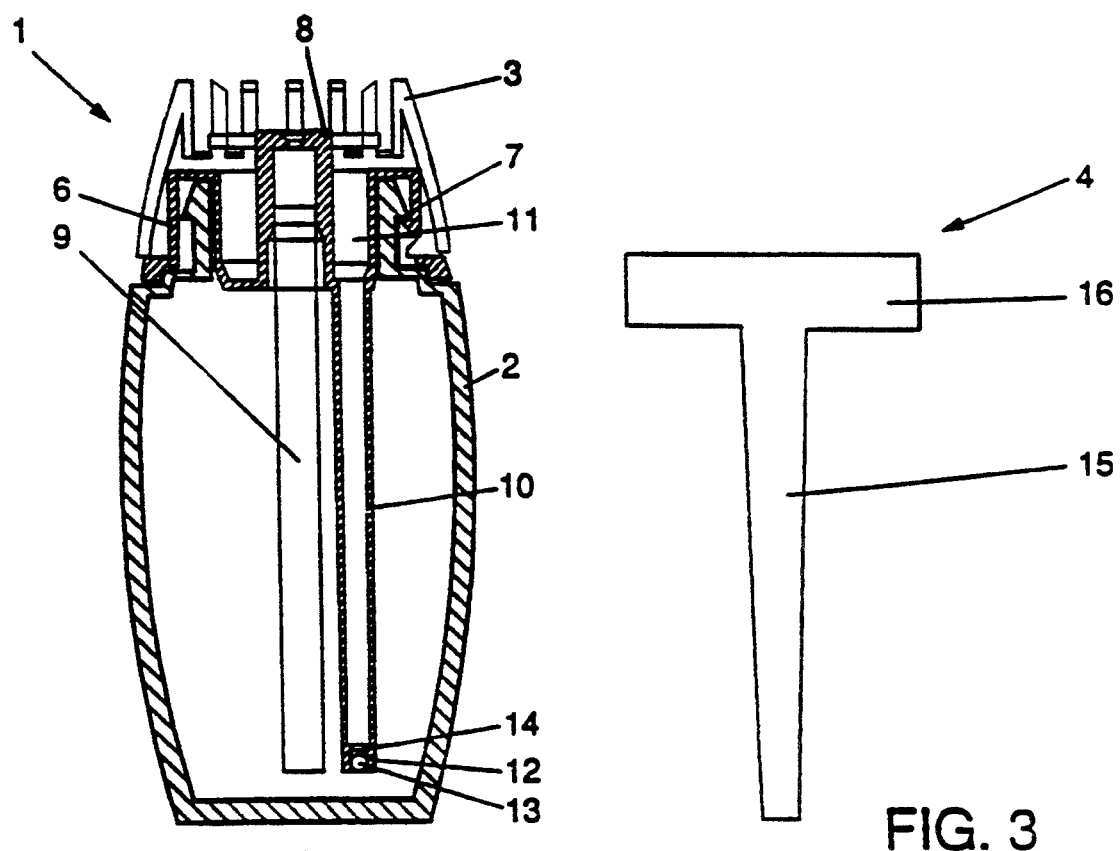
FIG. 2
FIG. 3

DISPENSER ADAPTED FOR COMBINED CONTINUOUS AND INSTANT OPERATION

This invention relates to a dispenser adapted for combined continuous and instant operation, i.e., a dispenser which continuously releases the active substance through absorption and evaporation, and, if so desired, can instantly release a large charge of the active substance.

Well known are dispensers that operate continuously through evaporation, which comprise a porous, absorbent medium and an evaporation surface, and are filled with a solution of an active substance, such as insecticide or a medicinal substance for medical applications, or with perfume or deodorant for cosmetic applications or use as an air-freshener.

Also known are spray dispensers adapted for instant operation, for instance a deformable squeeze-bottle having an immersion tube channel arranged therein, the liquid being sprayed by generating a pressure in the bottle and discharging liquid via the immersion tube. Prior to discharge, the liquid is mixed with air that is present in the bottle above the liquid. Aerosols are a variant of such dispensers.

The object of this invention is to provide a dispenser which combines the two above-described principles of operation and can be manufactured simply and economically.

This object is realized by providing a dispenser comprising a container which is to be partly filled with liquid active substance and has a wall that is at least locally resiliently deformable, with two immersion tube channels extending from a point adjacent the bottom of the container up to the top of the container, one channel terminating in a spray nozzle and the other channel containing a wick or similar absorbent material and terminating in an evaporation space that communicates with the atmosphere.

Active-substance containing liquid will be absorbed continuously via the wick and enabled to evaporate in the evaporation space communicating with the atmosphere. By squeezing the container, a large quantity of liquid can instantly be discharged via the spray nozzle.

Simple and economical manufacture can be realized by forming the spray nozzle, the evaporation space and at lease one of the immersion tube channels as a single moulding which can be snapped onto the mouth of the container so as to seal it.

In further elaboration of the invention, the spray nozzle and the evaporation space can be closed by one common cover so as to prevent evaporation before the dispenser pun into use.

Furthermore, in further elaboration of the invention, the spray nozzle may be formed substantially concentrically within the evaporation space and the wick may comprise an elongate portion extending in the corresponding immersion tube channel and a portion extending transverse thereto, extending around the spray nozzle in the evaporation space.

Such a, for instance T-shaped, wick can have its leg arranged in the corresponding immersion tube channel while the transverse portion is arranged around the spray nozzle in the evaporation space.

To prevent liquid being forced into the immersion tube channel containing the wick and thence into the evaporation space during the momentary generation of pressure in the container, the dimensions of the wick and those of the immersion tube channel containing the wick can be mutually adjusted in such a manner that the liquid cannot pass the wick in the immersion tube.

Another way of preventing the liquid from flowing upward through the immersion tube channel during the momentary generation of pressure, is to arrange a non-return valve element in the lower part of the immersion tube, this valve element being formed, for instance, by a ball that is mounted with radial clearance in the lower part of the immersion tube channel and confined with axial clearance by two constrictions provided in the channel, the upper constriction forming a valve seat for the ball, so that the channel is shut off when the pressure in the container rises, while any excess liquid in the evaporation space can flow back into the container. To clarify the invention, one embodiment will now be discussed, by way of example, with reference to the accompanying drawings, in which:

FIG. 1 is a longitudinal section of the dispenser;
FIG. 2 is a cross-section of the dispenser; and
FIG. 3 is a side elevation of the wick.

The dispenser 1 of the embodiment shown, which may for instance serve as an air-freshener, comprises a container 2, an upper cap 3, a wick 4, a cover 5, which is partly shown on the left-hand side of FIG. 1 and serves to close the dispenser before it is put into use, and a plug 6. The plug 6 is a single molding and is secured onto the mouth of container 2 by means of a snap connection 7 and comprises a spray nozzle 8 from which extends an immersion tube channel 9 to a point adjacent the container bottom. Further, the plug 6 comprises a second immersion tube channel 10 extending from an evaporation space 11, provided around the spray nozzle, down to a point adjacent the bottom of the container. Arranged in the lower end of the immersion tube channel 10 is a non-return valve element 12. The non-return valve 12 in the embodiment shown is designed as a ball 13, incorporated with radial clearance in the lower part of the immersion tube channel 10 and confined with axial clearance by two constrictions provided in the channel 10, the upper constriction forming a valve seat 14 for the ball 13, so that the channel 10 is shut off when the pressure in the container 2 rises.

The wick 4 is made of porous, liquid-absorbent material and T-shaped. For the sake of clarity, the wick 4 is not shown in FIGS. 1–2. When the wick 4 is disposed in the dispenser 1, the leg 15 of the T-shaped wick 4 is disposed in the immersion tube 10 and the crosspiece 16 of the T-shaped wick 4 is disposed around the spray nozzle 8 against the inside of the wall bounding the evaporation space 11. The crosspiece 16 forms the evaporation surface of the wick 4.

It will be clear that the invention is not limited to the embodiment described, but that various modifications are possible within the framework of the invention. Essential to the present invention is that a dispenser is provided which combines instant operation with a continuous operation that provides a background fragrance.

I claim:

1. A dispenser comprising a container which is to be partly filled with liquid active substance and has a wall that is at least locally resiliently deformable, said dispenser further comprising two immersion tube channels extending from a point adjacent the bottom of the container up to the top of the container, one channel terminating in a spray nozzle and the other channel containing a wick and terminating in an evaporation space that communicates with the atmosphere.

2. A dispenser according to claim 1, characterized in that the spray nozzle, the evaporation space and at least one of the immersion tube channels are formed as a single molding which can be click-fitted onto a mouth of the container so as to seal therebetween.

3. A dispenser according to claim 2, characterized in that the spray nozzle and the evaporation space are closeable by a common cover.

4. A dispenser according to claim 3, characterized in that the spray nozzle is formed substantially concentrically within the evaporation space and the wick comprises an elongate portion extending in the corresponding immersion tube channel and a portion extending transverse thereto, extending around the spray nozzle in the evaporation space.

5. A dispenser according to claim 4 characterized in that a non-return valve element is arranged at the lower end of the channel containing the wick.

6. A dispenser according to claim 5, characterized in that the non-return valve element is formed by a ball which is arranged with radial clearance in the lower part of the channel and confined by two constrictions provided in the channel, the upper of the two constrictions forming a valve seat for the ball.

* * * * *